(12) United States Patent
Ralph et al.

(10) Patent No.: US 9,814,577 B2
(45) Date of Patent: Nov. 14, 2017

(54) IMPLANTABLE MESH FOR MUSCULOSKELETAL TRAUMA, ORTHOPEDIC RECONSTRUCTION AND SOFT TISSUE REPAIR

(75) Inventors: James D. Ralph, Bethlehem, PA (US); Thomas N. Troxell, Pottstown, PA (US); Mark Michels, Glen Mills, PA (US)

(73) Assignee: BioDynamics LLC, Englewood, NJ (US)

( * ) Notice: Subject to any disclaimer, the term of this patent is extended or adjusted under 35 U.S.C. 154(b) by 0 days.

(21) Appl. No.: 13/040,072

(22) Filed: Mar. 3, 2011

(65) Prior Publication Data

US 2011/0152865 A1 Jun. 23, 2011

Related U.S. Application Data

(63) Continuation of application No. 11/779,559, filed on Jul. 18, 2007, now abandoned.

(51) Int. Cl.
*A61B 17/80* (2006.01)
*A61F 2/28* (2006.01)
(Continued)

(52) U.S. Cl.
CPC ........ *A61F 2/2846* (2013.01); *A61B 17/8028* (2013.01); *A61B 17/8085* (2013.01); *A61F 2/36* (2013.01); *A61F 2002/2817* (2013.01); *A61F 2002/30014* (2013.01); *A61F 2002/30032* (2013.01); *A61F 2002/30062* (2013.01); *A61F 2002/30235* (2013.01); *A61F 2002/30293* (2013.01); *A61F 2002/30909* (2013.01); *A61F 2002/30914* (2013.01); *A61F 2002/30915* (2013.01); *A61F 2002/30968* (2013.01); *A61F 2002/4495* (2013.01); *A61F 2210/0004* (2013.01); *A61F 2230/0069* (2013.01); *A61F 2230/0091* (2013.01);
(Continued)

(58) Field of Classification Search
CPC ........ A61B 17/80; A61B 17/8028; A61F 2/36
USPC ........ 606/70, 71, 280–299, 76–78; 623/17.11–17.16
See application file for complete search history.

(56) References Cited

U.S. PATENT DOCUMENTS

| 1,156,440 A | 10/1915 | Smith |
| 3,040,741 A | 6/1962 | Carolan |

(Continued)

FOREIGN PATENT DOCUMENTS

JP 11-056862 3/1999

OTHER PUBLICATIONS

Keskin et al, Collagen-chondroitin sulfate-based PLLA-SAIB-coated rhBMP-2 delivery system for bone repair; Biomaterials 26 (2005) 4023-4034, available online Nov. 13, 2004 (Introduction; Fig. 4).
(Continued)

*Primary Examiner* — Christopher Beccia
(74) *Attorney, Agent, or Firm* — Lowenstein Sandler LLP

(57) ABSTRACT

Biocompatible mesh materials are employed to make implants for repairing or replacing a bone or for soft tissue repair. The mesh materials can be comprised of bioabsorbable materials, non-bioabsorbable materials or bioabsorbable and non-bioabsorbable materials. Pharmaceutical actives, bone growth enhancers and the like can be combined with the implants.

13 Claims, 28 Drawing Sheets

(51) Int. Cl.
*A61F 2/36* (2006.01)
*A61F 2/30* (2006.01)
*A61F 2/44* (2006.01)

(52) U.S. Cl.
CPC . *A61F 2250/003* (2013.01); *A61F 2250/0018* (2013.01); *A61F 2310/00011* (2013.01); *A61F 2310/00365* (2013.01)

(56) References Cited

U.S. PATENT DOCUMENTS

| | | | |
|---|---|---|---|
| 3,463,158 A | | 8/1969 | Schmitt et al. |
| 3,710,789 A | | 1/1973 | Ersek |
| 4,883,486 A | | 11/1989 | Kapadia et al. |
| 5,139,497 A | | 8/1992 | Tilghman et al. |
| 5,139,528 A | | 8/1992 | Koch et al. |
| 5,195,542 A | | 3/1993 | Gazielly et al. |
| 5,368,602 A | * | 11/1994 | de la Torre ............ 606/151 |
| 5,397,359 A | * | 3/1995 | Mittelmeier et al. ...... 623/23.54 |
| 5,443,483 A | | 8/1995 | Kirsch |
| 5,468,242 A | | 11/1995 | Reisberg |
| 5,549,619 A | | 8/1996 | Peters et al. |
| 5,779,706 A | * | 7/1998 | Tschakaloff ....... A61B 17/8085 219/229 |
| 5,824,088 A | * | 10/1998 | Kirsch ................ A61B 17/80 424/423 |
| 5,948,020 A | | 9/1999 | Yoon et al. |
| 5,980,540 A | | 11/1999 | Bruce |
| 6,071,291 A | | 6/2000 | Forst et al. |
| 6,113,640 A | | 9/2000 | Tormala et al. |
| 6,232,354 B1 | | 5/2001 | Tan |
| 6,280,473 B1 | | 8/2001 | Lemperle et al. |
| 6,391,059 B1 | | 5/2002 | Lemperle et al. |
| 6,391,060 B1 | * | 5/2002 | Ory et al. ................ 623/23.76 |
| 6,497,728 B2 | * | 12/2002 | Yong ......................... 623/23.46 |
| 6,585,769 B1 | * | 7/2003 | Muhanna et al. ......... 623/13.14 |
| 2002/0123750 A1 | | 9/2002 | Eisermann et al. |
| 2002/0173854 A1 | | 11/2002 | Amrich |
| 2005/0015154 A1 | | 1/2005 | Lindsey et al. |
| 2005/0043733 A1 | * | 2/2005 | Eisermann ............ A61B 17/68 623/17.11 |
| 2005/0054998 A1 | * | 3/2005 | Poccia, III ........ A61F 13/15699 604/367 |
| 2005/0260247 A1 | | 11/2005 | Ralph et al. |
| 2005/0283255 A1 | | 12/2005 | Geremakis et al. |
| 2006/0264948 A1 | * | 11/2006 | Williams ............... A61B 17/70 606/71 |
| 2007/0270812 A1 | * | 11/2007 | Peckham ............ A61B 17/7059 606/279 |
| 2008/0004714 A1 | * | 1/2008 | Lieberman ............ A61B 17/58 623/23.76 |
| 2008/0262630 A1 | * | 10/2008 | Fulmer .................... A61F 2/06 623/23.52 |

OTHER PUBLICATIONS

Supplementary European Search Report dated Jun. 25, 2013.

* cited by examiner

127 FIG. 9E

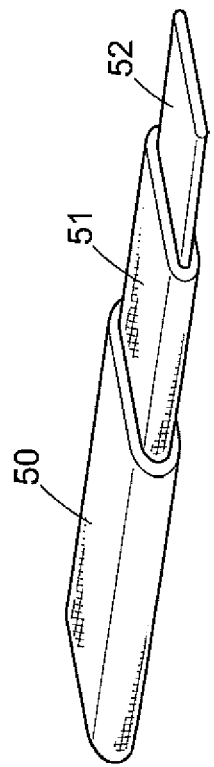
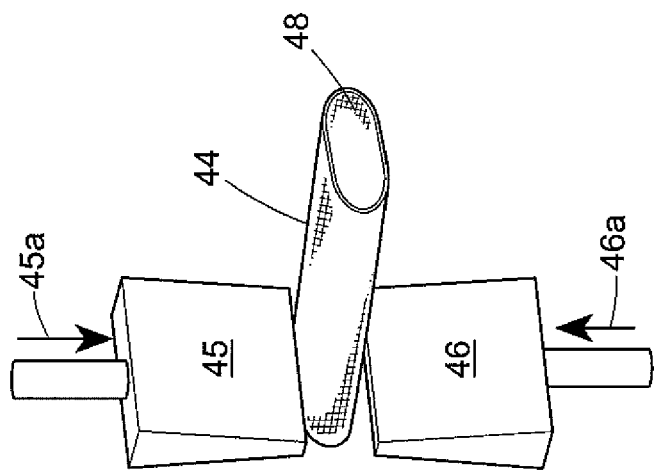

IMPLANTABLE MESH FOR MUSCULOSKELETAL TRAUMA, ORTHOPEDIC RECONSTRUCTION AND SOFT TISSUE REPAIR

BACKGROUND OF THE INVENTION

Field of the Invention

The present invention relates to biocompatible mesh materials that are formed into implantable structures for treatment of musculoskeletal trauma, orthopedic reconstruction and soft tissue applications.

The Related Art

Biocompatible mesh materials have traditionally been used in soft tissue surgery. But these materials have been largely ignored for skeletal repair, due in part to their flexibility and lack of strength. For example, U.S. Pat. No. 3,463,158 describes polyglycolic acid materials which are used to make absorbable and partially absorbable woven devices which are said to be useful in the repair of hernias, arteries and veins.

More rigid hardware devices made from fenestrated shells are described in U.S. Patent Application Pub. No. 2005/0015154. These devices are said to enhance tissue integration so that the device becomes permanently affixed to the tissue.

There are many musculoskeletal trauma and orthopedic reconstruction needs that are not effectively met by current technology either because the materials of construction are too rigid or too flexible for their designated applications. The devices of the present invention provide a significant improvement over the current technology by employing mesh materials in a non-traditional manner and/or by employing certain new mesh materials and modified mesh materials in medical applications.

SUMMARY OF THE INVENTION

The implantable devices of the present invention employ meshes comprised of bioabsorbable materials or non-bioabsorbable materials or a combination of bioabsorbable and non-bioabsorbable materials. Each device is made in the form of a structure having the strength and other physical characteristics necessary to carry out its intended purpose. The meshes can be employed alone to form implantable devices or they can be combined with other and different meshes and/or non-mesh materials to form implantable devices. The devices also can be combined with pharmaceutical agents, bone growth enhancers and the like.

Mesh materials, which can be used in the present invention, can take numerous forms. They can be woven, knitted, braided or knotted, or an arrangement of interlocking links (such as the links of the type found in jewelry or chain link fencing) or other interlocking, intertwined or interwoven constructions and the terms "mesh" or "mesh materials" as used herein are intended to include these various forms and constructions.

BRIEF DESCRIPTION OF THE DRAWINGS

The figures illustrate mesh materials employed in the invention and embodiments of the invention employing the mesh materials. The figures may not be drawn to scale.

FIG. 9E illustrates a mesh in an interlocking link configuration.

FIGS. 13B-1, 13B-2 and 13B-3 illustrate tubular forms of woven meshes which have been rolled upon themselves.

FIG. 14A illustrates a section of tubular mesh to be sealed at one or both ends.

FIGS. 14B-1 and 14B-2 illustrate a multi-component flattened tubular mesh construct.

FIGS. 14B-3 and 14B-4 illustrate a resected rib segment which is repaired using flattened tubular mesh.

FIGS. 14D-1 and 14D-2 illustrate an inner mesh member formed into a loop and adjusted through a tubular mesh member.

FIG. 14D-3 illustrates a mesh strap with a fastener affixed to one end.

FIGS. 14E-1 and 14E-2 illustrate flattened tubular mesh covering a bone plate.

FIGS. 14E-3, 14E-4 and 14E-5 illustrate bone plates having mesh material laminated thereon;

FIGS. 16B-1, B-2, B-3 and B-4 illustrate a sequence using a rolled pre-shaped mesh sheet to make a hip stem.

FIGS. 16C-1, C-2, C-3 and C-4 illustrate the use of mesh and a core member to make a hip stem.

DETAILED DESCRIPTION OF THE INVENTION

The invention has to do with implantable devices made from mesh materials. One or more than one type of mesh material can be used in an implantable device of the invention. And the mesh material can be combined with non-mesh materials such as rods, tubes, solid sheets, perforated sheets, fillers and other materials of various shapes, forms and compositions to make a composite implant structure having sufficient strength to carry out its intended purpose. The implantable devices of the invention can be used to repair or replace a bone or a joint or reattach a tendon, muscle or cartilage. Novel mesh structures for soft tissue repair are also described.

Figure 1:
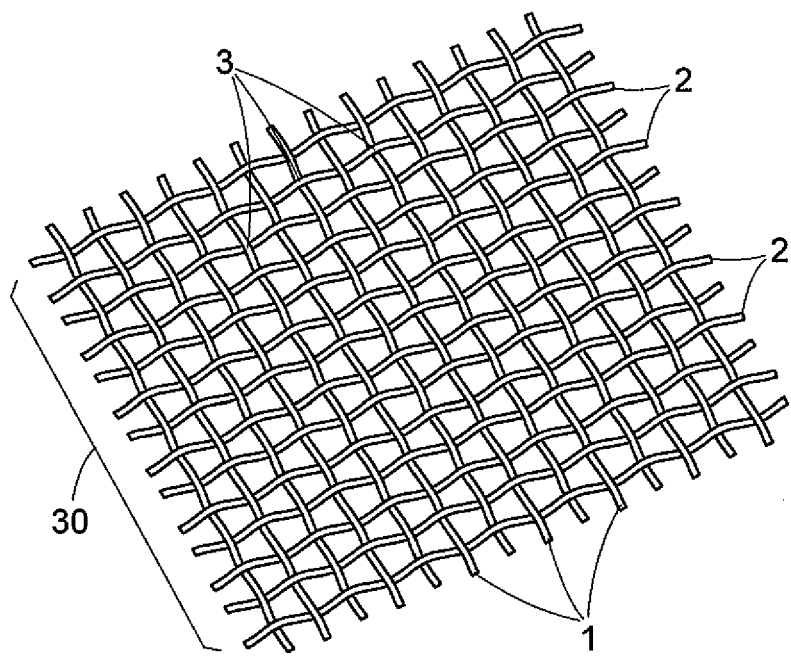
FIG. 1 illustrates a simple implantable mesh.

In the simplest structure, a woven implantable mesh consists of two sets of strands crossed over and under each other in a simple alternating pattern as shown in FIG. 1. Strands 1 are approximately perpendicular to strands 2 and they intersect at points of contact 3.

Figure 2:
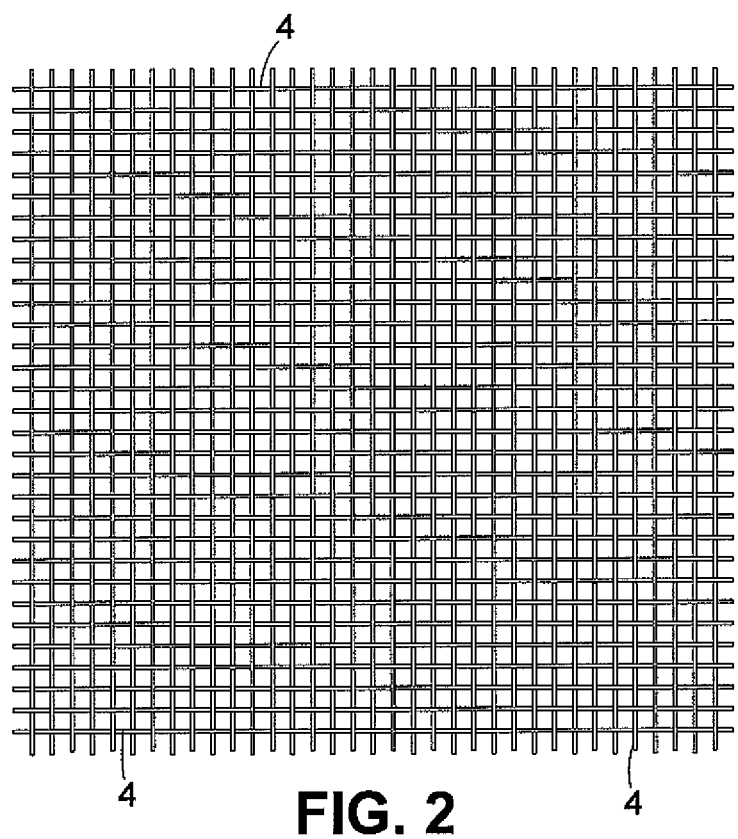
FIG. 2 illustrates the type of mesh shown in FIG. 1 in a more dense weave with smaller voids.

Many other woven mesh configurations are possible, however. Decreasing the spacing between the strands can produce a denser, less permeable mesh with smaller voids 4 as shown in FIG. 2. These voids can be precisely tailored either to encourage or discourage hard or soft tissue ingrowth.

Figure 3:
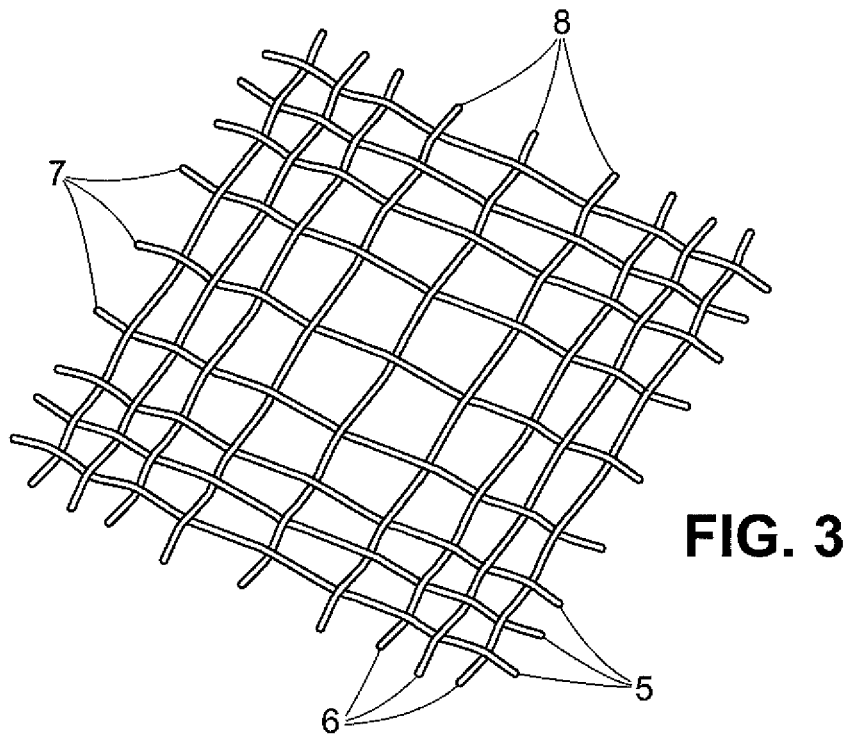
FIG. 3 illustrates a mesh with variable spacing between strands.

The mesh can also be woven with a variable spacing between strands. This can occur along one axis or along both as shown in FIG. 3 wherein strands 5 and strands 6 are closely spaced along both axes as compared with strands 7 and strands 8. This concept is subject to numerous variations as will be apparent to those having skill in the art.

Figure 4:
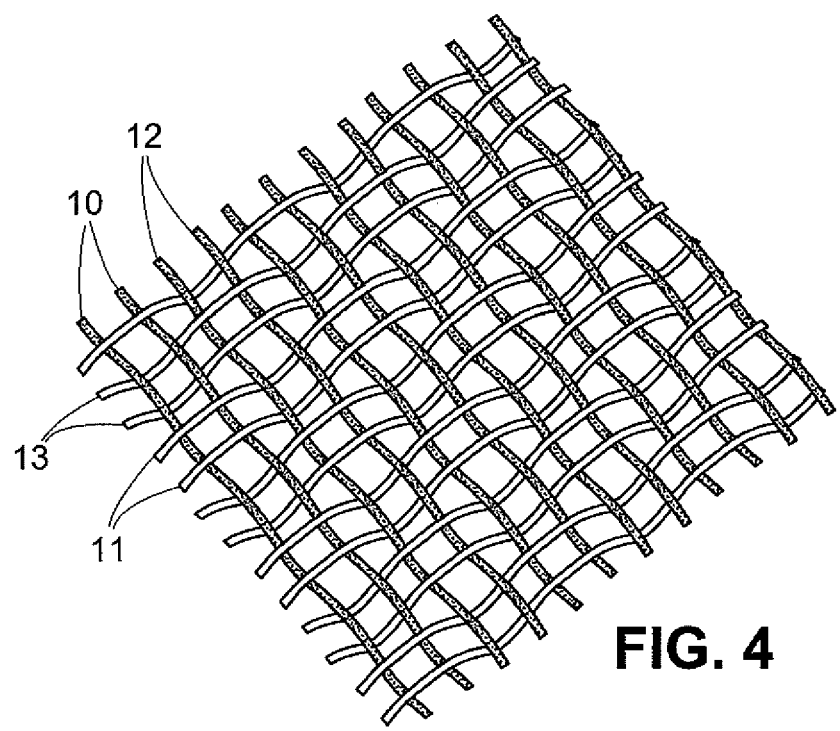
FIG. 4 illustrates a loosely woven mesh having alternating pairs of strands in each direction.

A loosely woven mesh can be created by alternating pairs of strands in each direction as shown in FIG. 4 where strand pair 10 alternates with strand pair 12 along one axis and strand pair 11 alternates with strand pair 13 along another axis. Variations of this include double strands along only one axis and one strand or numbers of strands greater than two in any direction.

Figure 5:
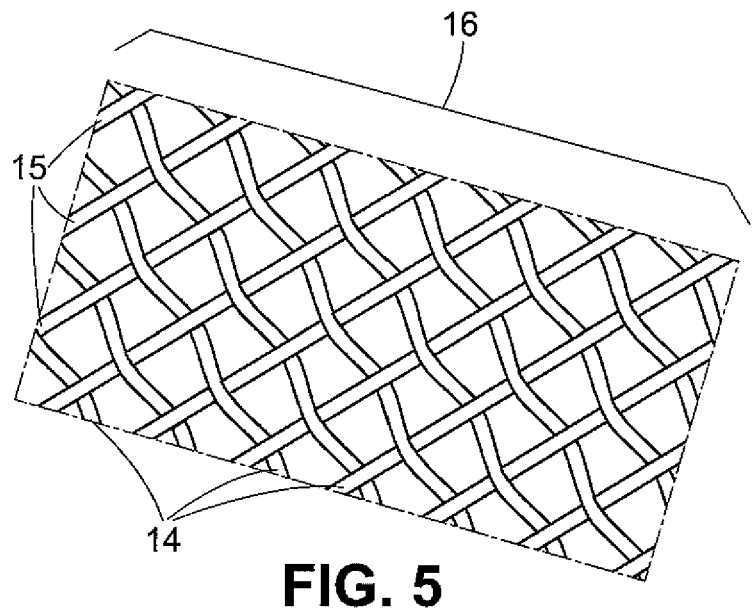
FIG. 5 illustrates a mesh wherein the strands are not parallel to the edges of the sheet.

All of the above examples show the strands essentially parallel to the edges of the sheet of mesh, but this too can be varied as shown in FIG. 5 wherein all of the strands 14 and 15 are not parallel to the edges of the sheet of mesh 16.

Figure 6:
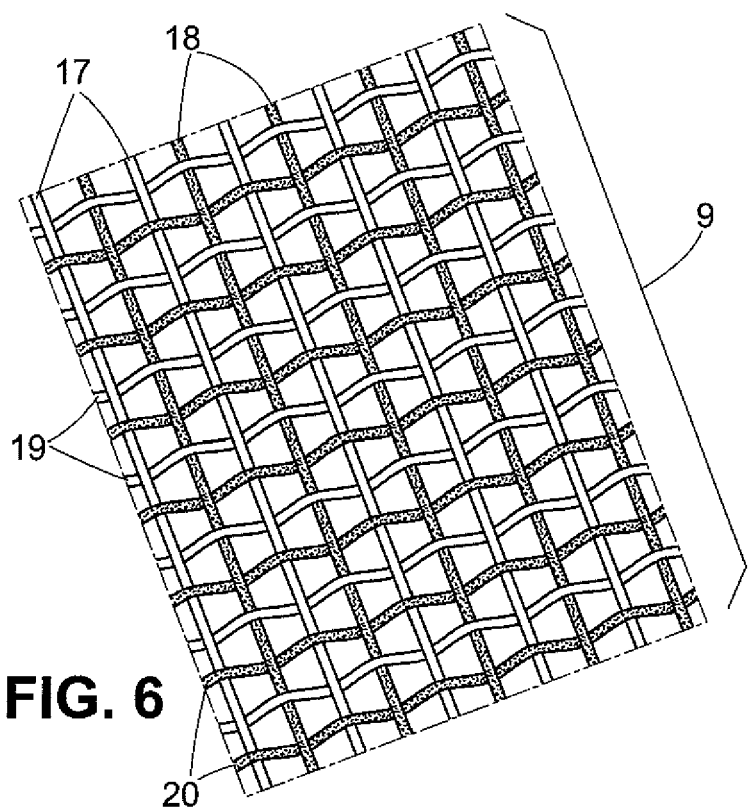
FIG. 6 illustrates a mesh with alternating pairs of strands.
Figure 7:
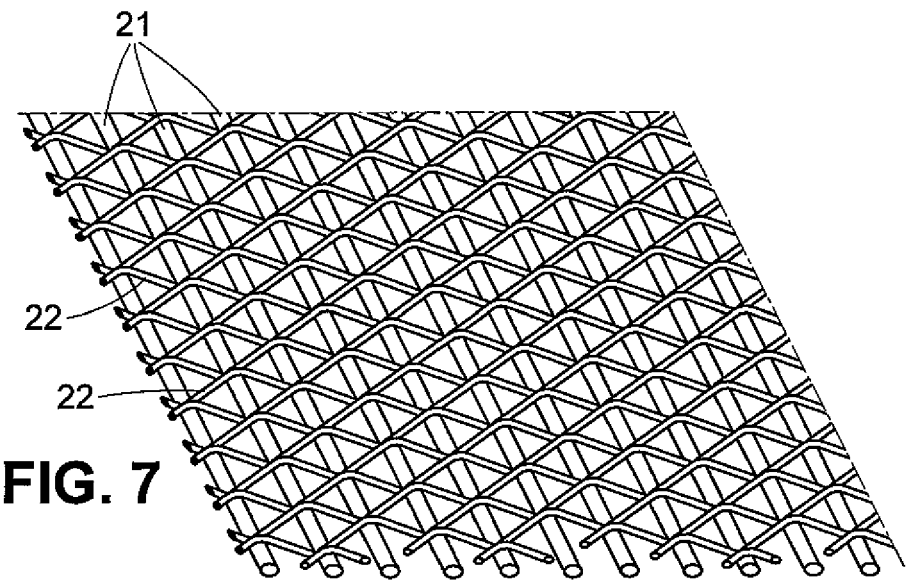
FIG. 7 illustrates a mesh having different strands in different dimensions.

By varying the fibers or strands in each direction, the material properties can be changed uniformly as shown in FIG. 6 or distinctly different directional properties can be created as shown in FIG. 7. In mesh 9 of FIG. 6, relatively stiff strands 17 are alternated with relatively flexible strands 18 along one axis and strands of one material 19 are alternated with strands of another material 20 along the other axis. In FIG. 7, relatively stiff strands 21 are along one axis and flexible strands 22 are along the other. These various configurations can be used to vary physical properties of the mesh material, such as directions of bending and strength, as well as other properties such as by alternating bioabsorable and non-bioabsorbable materials.

Figure 8:
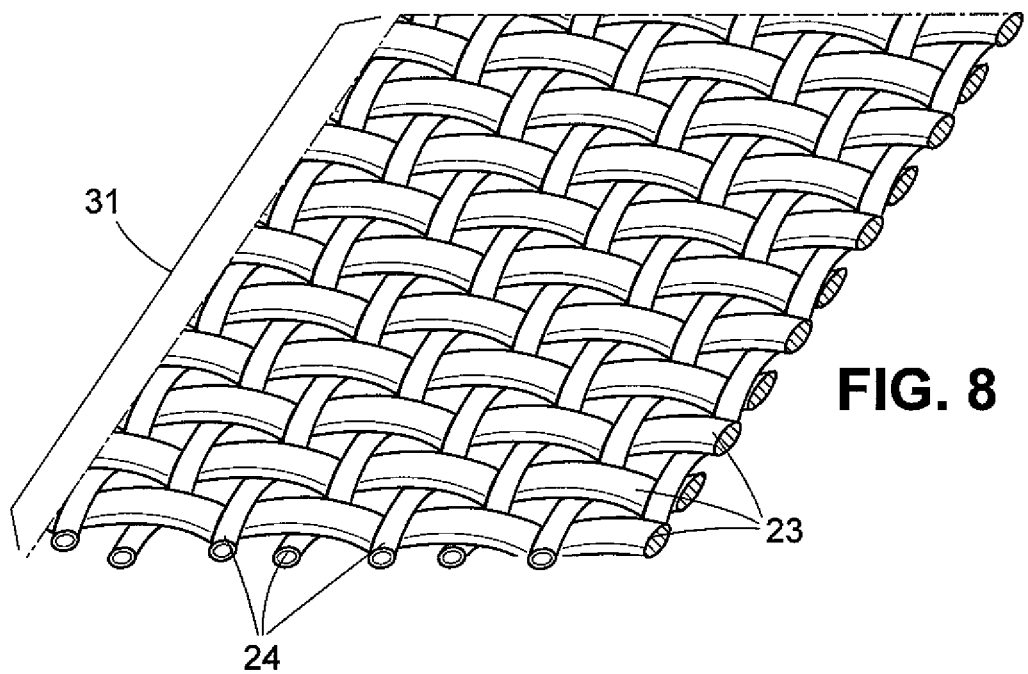
FIG. 8 illustrates a mesh with solid oval strands in one direction and hollow round strands in the other.

FIGS. 1-7 show essentially round strands but they could also be flattened strips or intermediate shapes such as ovals. FIG. 8 shows a mesh with solid oval strands 23 in one direction and hollow round strands 24 in the other.

Figure 9A:
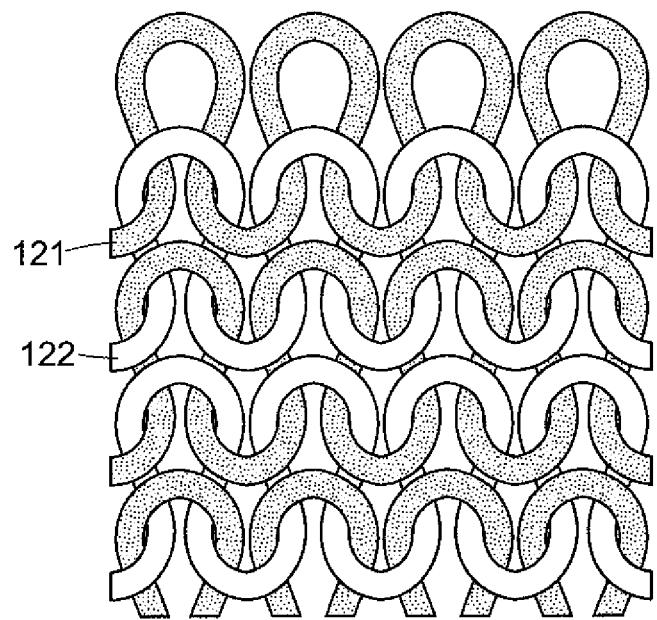
FIGS. 9A and 9B illustrate meshes which are knitted.
Figure 9B:
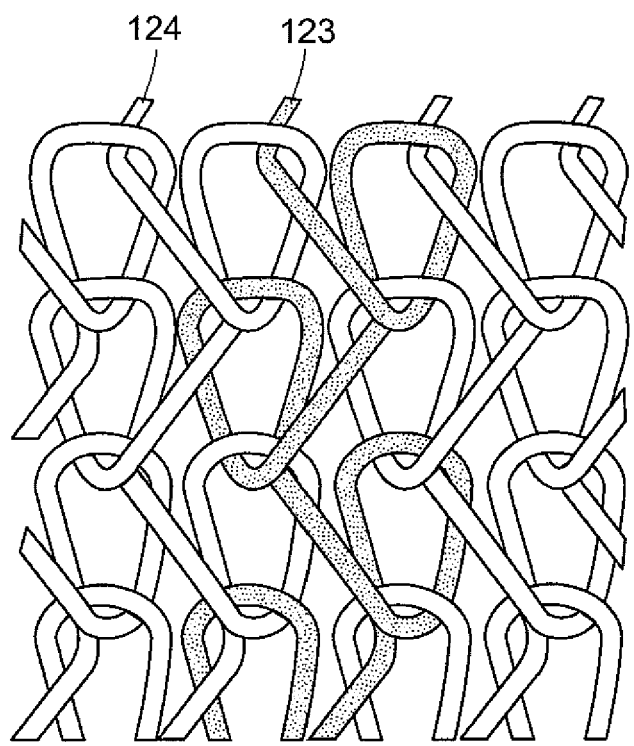
Figure 9C:
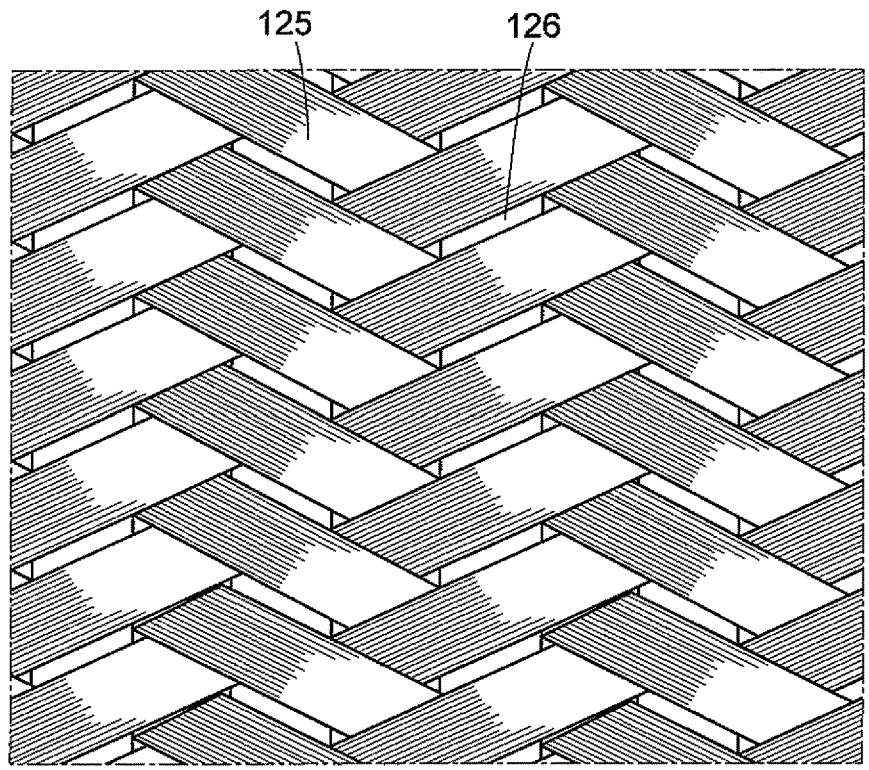
FIG. 9C illustrates a braided mesh.
Figure 9D:
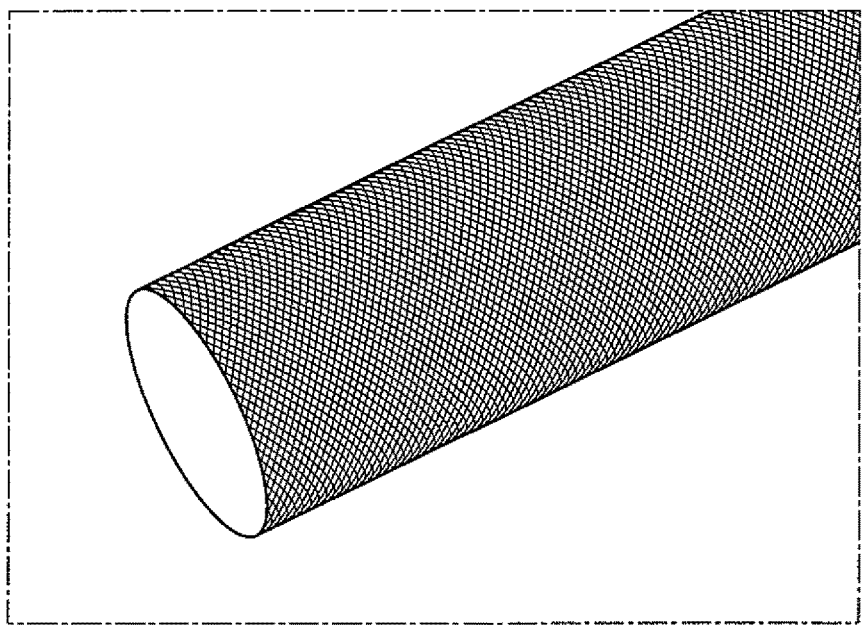
FIG. 9D illustrates a tubular braided mesh.
Figure 9F:
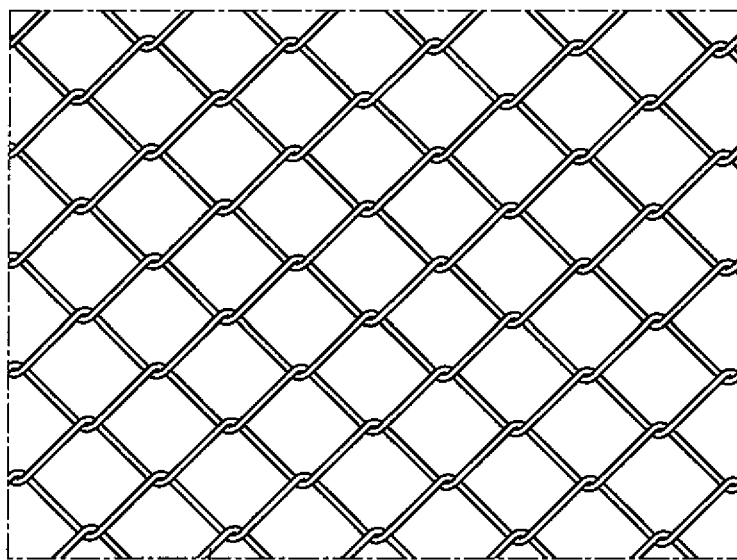
FIG. 9F illustrates a knotted mesh.
Figure 9F:
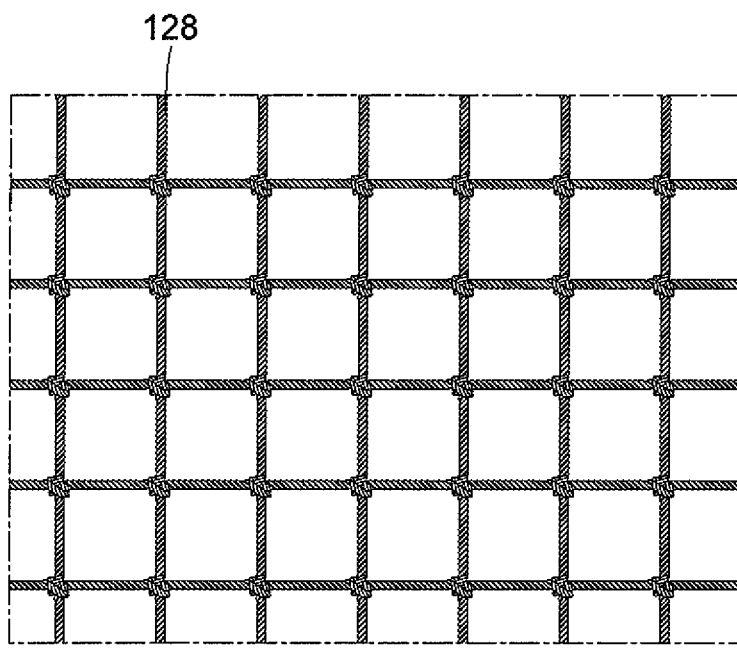

Numerous other constructions can be used to make the mesh materials of the present invention as will be apparent to those skilled in the art based upon the disclosures herein. Some examples are provided in FIGS. 9A-9F. FIGS. 9A and 9B illustrate different types of knitted mesh. In FIG. 9A, strands 121 and 122 are illustrated in a weft-knitted construction. FIG. 9B illustrates a warp-knitted construction with strands 123 and 124. FIG. 9C shows a braided mesh using flat strands 125 and 126. Of course, tubular braided mesh can be made, for example, following the construction of the braided shield for coaxial cable as illustrated in FIG. 9D. FIG. 9E illustrates a mesh having an interlocking link configuration using strands 127. A knotted mesh with strands 128 is illustrated in FIG. 9F.

The strand materials can come from any of the classes of biocompatible implant materials; metallics, bioresorbable polymers and non-resorbable polymers. In addition, organic materials such as collagen are suitable in some applications. The strands can have various physical structures. For example, they can be monofilament or thread or yarn structures. They can be braided or they can be hollow tubular structures and the hollow tubular structures can have a cross-section which is round, oval, square, rectangular, triangular or of any other closed geometric shape, including irregular shapes. If the hollow strands are porous or biodegradable, they can be filled with medication or bone growth substances to provide a timed release at the surgical site. A surgical mesh which incorporates a timed release of antibiotics is particularly attractive in abdominal wall or hernia repair.

Figure 10A:
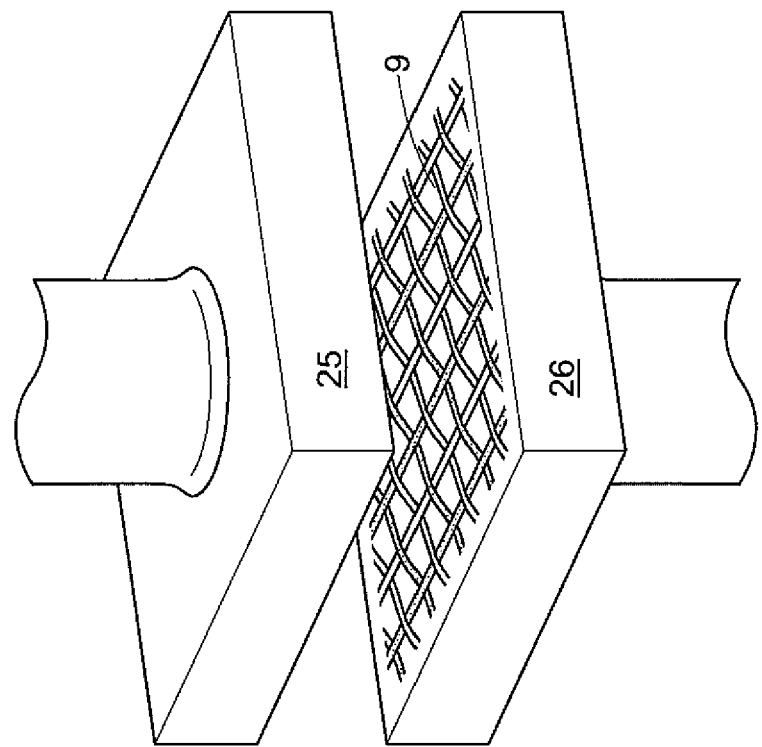
FIG. 10A illustrates a mesh with strands of different materials between two heated platens.
Figure 10:
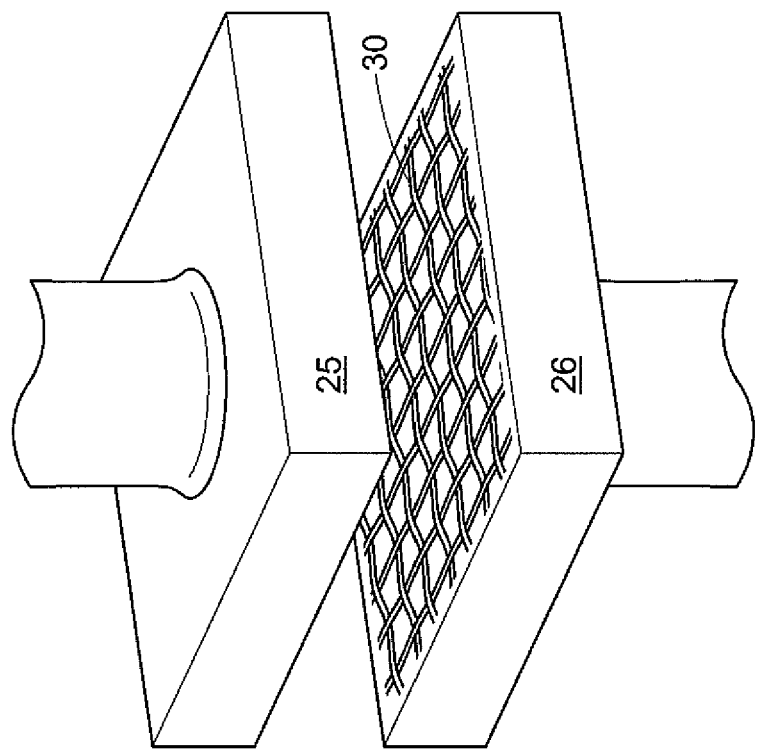
FIG. 10 illustrates a mesh between two heated platens.

Many of the previous examples show a woven mesh in a flat configuration but this is just the starting point for mesh implants. In a flat woven configuration, the individual strands can shift relative to each other to provide maximum flexibility. In other applications it might be desirable to constrain the strands to create a more rigid construction. This can be accomplished in several ways. One method is to sinter the woven mesh. Sintering is the process of fusing adjacent structures by heating them just below the melting point of the material. At this temperature the strands will soften and fuse together where they contact one another. Pressure may be used in addition to heat alone. FIG. 10 illustrates a basic mesh 30, as illustrated in FIG. 1, between two heated platens 25 and 26. Because the strands are of the same material in both directions, the resulting mesh will be fused at each point of contact where the strands cross one another (i.e., at the intersections). Of course, adhesives, knots or other means known to those having skill in the art can be used to adhere the strands to one another at points of contact.

If this same process is applied to mesh 9 shown in FIG. 6, where the alternating strands in both directions are of different materials, the resulting mesh will have different characteristics. If strands 18 and 20 have a lower melting point than strands 17 and 19, then heating the platens to just below the strands 18 and 20 melting point will cause only the strands 18 and 20 to fuse to one another at their intersections. The strands 17 and 19 will remain mobile relative to one another and relative to the strands 18 and 20. FIG. 10A illustrates this concept. Variations on this concept would include a mesh material wherein most of the strands have a lower melting point than the others or wherein most of the strands have a higher melting point than the others. The lower melting point strands can be dispersed evenly, unevenly or in a specific woven pattern. One lower melting point strand or one higher melting point strand could be woven in a manner that would cause it to have one or more than one point of contact with itself, such as a woven loop. Thus, a sintered mesh material according to the invention could comprise higher melting point strands and at least one lower melting point strand having one or more than one point of contact with itself or two or more than two lower melting point strands having at least one of point of contact wherein the lower melting point strand or strands are sintered, and therefore affixed, at the point or points of contact.

Figure 11:
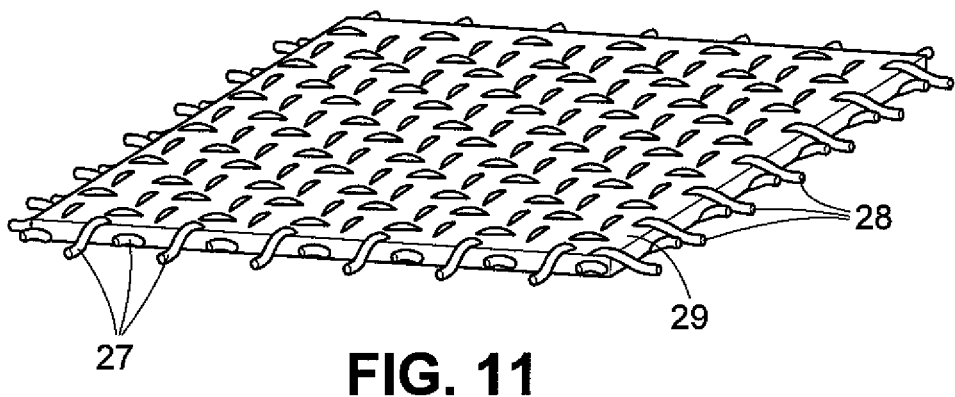
FIG. 11 illustrates a filled mesh.

Another method of constraining the strands in a mesh is to fill the interstices between the strands with another biocompatible material thereby locking the strands in their relative positions. This also serves to combine the properties of the mesh material and the filler. In this manner, the mesh structure can act as a reinforcing element for the filler resulting in a composite material having properties superior to either material alone. Suitable filling materials include resorbable polymers, hydrogels, collagen as well as non-resorbable polymers. If this material is bioresorbable, then the gradual degradation of the bioresorbable component will alter the overall mechanical properties of the filled mesh over time. If the filling material is non-resorbable, then the mechanical properties will remain unchanged after implantation. A filling material that softens at a relatively low temperature (like most bioresorbable polymers) also provides the advantage of allowing the mesh to be shaped intraoperatively. In surgery, it is often necessary to contour an implant to match the patient's anatomy and have the implant maintain the new contour while providing support to the tissue. Most polymer based meshes can be contoured but have the tendency to spring back to their original shape. Filling the mesh with a material that softens at a low temperature allows the implant to be heated in the operating room, contoured to fit the patient and then, after cooling, it maintains that form because the filler locks the strands in their new positions. FIG. 11 illustrates a filled woven mesh comprised of strands 27, strands 28 and filling material 29. This feature of intraoperatively reshaping an implant device is applicable to all of the embodiments of the invention wherein the materials used to make the implant (e.g., a mesh material, a combination of mesh materials or a combination of mesh material and non-mesh material) can be reshaped upon heating to a new contour that fits a patient's anatomy and the implant device maintains the new contour upon cooling.

Figure 12:
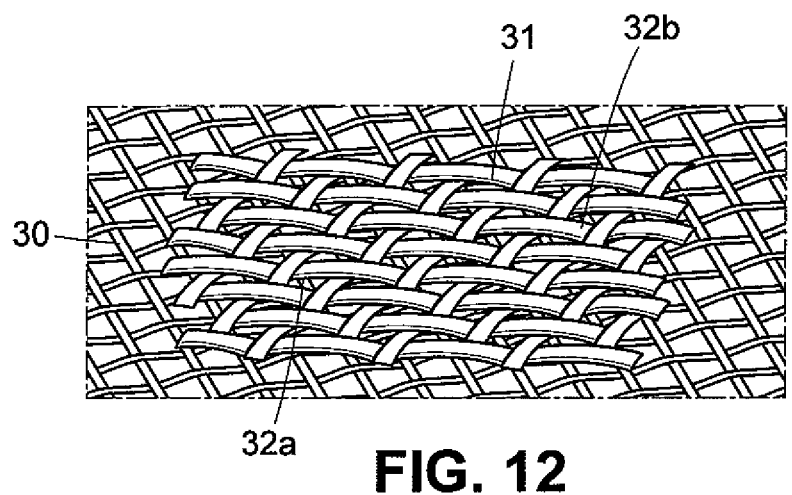
FIG. 12 illustrates two different meshes laminated together.

Implantable meshes can also be comprised of at least two sheets of mesh optionally adhered to one another, for example, laminated together or adhered to one another at predetermined discreet points of contact such as at points 32a and 32b in FIG. 12. The layers in a laminated construction can be multiple layers of the same mesh or they can be comprised of layers of different mesh materials. In addition, the orientation of the strands can remain constant or be varied from layer to layer. FIG. 12 illustrates one possible configuration where only two layers are shown for clarity, the layers being comprised of the mesh 30 of FIG. 1 and the mesh 31 of FIG. 8. Just as with a single layer of mesh, it is possible to sinter the mesh layers together (at predetermined discreet points of contact or at all points of contact) and/or fill them with another material.

Figure 12A:
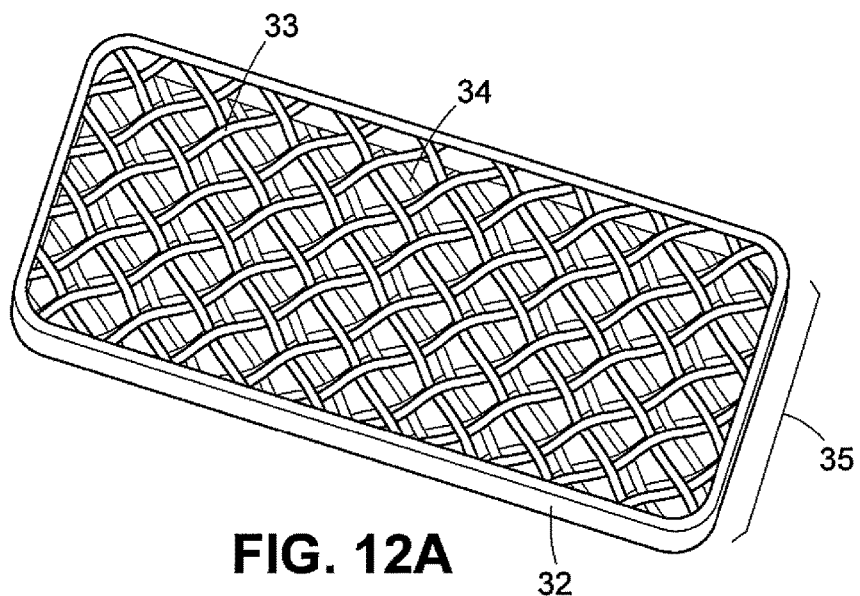
FIG. 12A illustrates two different meshes layered one on the other and having filled or sintered edges.

In another embodiment, a multilayer construction can have only the edges (i.e., the perimeter) sintered, filled or both. The center section remains flexible. An example is shown in FIG. 12A wherein a filling material 32 is applied around the edges of layered meshes 33 and 34 to make a layered mesh composite 35.

Figure 12B:
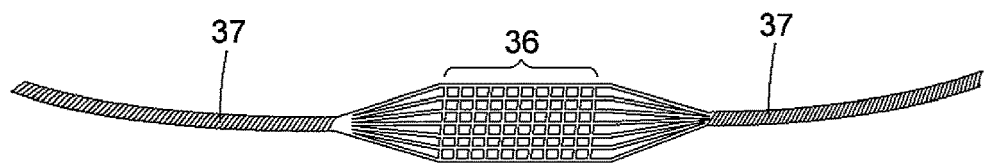
FIG. 12B illustrates a mesh having a variable shape.

Implantable mesh products can be produced in shapes other than flat sheets. FIG. 12B depicts a flat central section 36 which then tapers to a smaller, cable-like cross section 37 at each end (i.e., the opposing ends). The cable-like cross-section can also be described as a rope or strap and this portion of the device is made from the same material as the mesh material. Such a construct may be attached to a needle and sutured around bone or soft tissue to provide a larger area of support where required.

Figure 13:
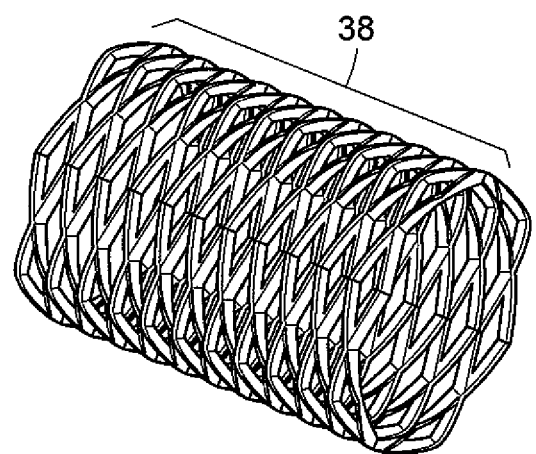
FIG. 13 and FIG. 13A illustrate tubular forms of meshes.
Figure 13A:
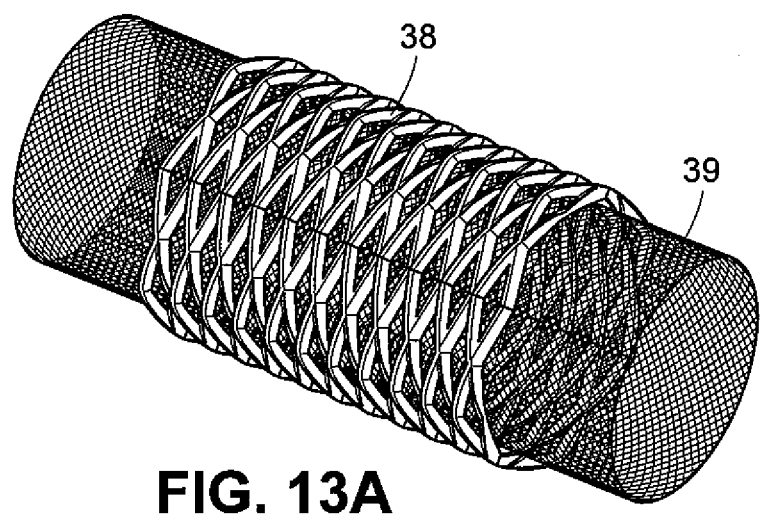
Figures 1, 13B:
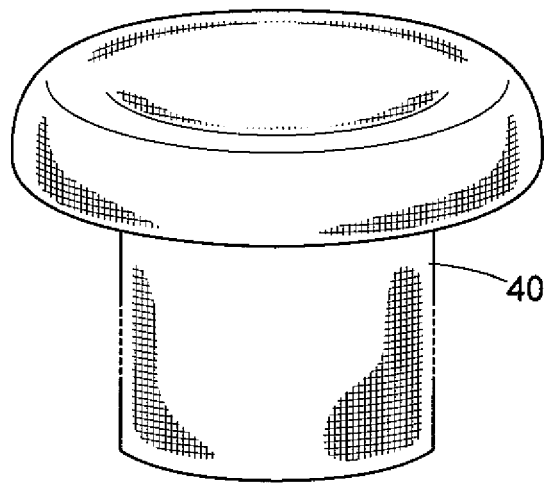
Figures 2, 13B:
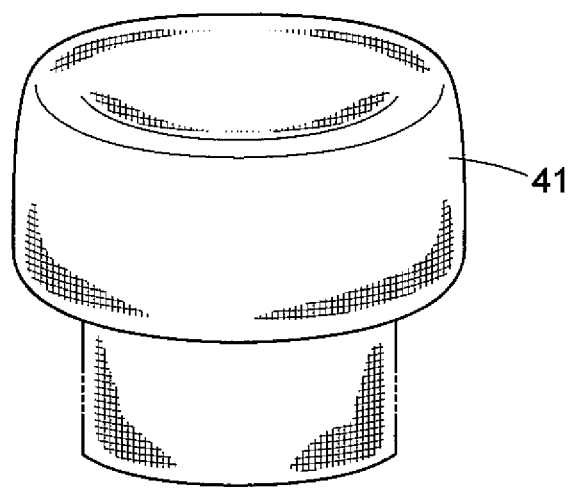
Figures 3, 13B:
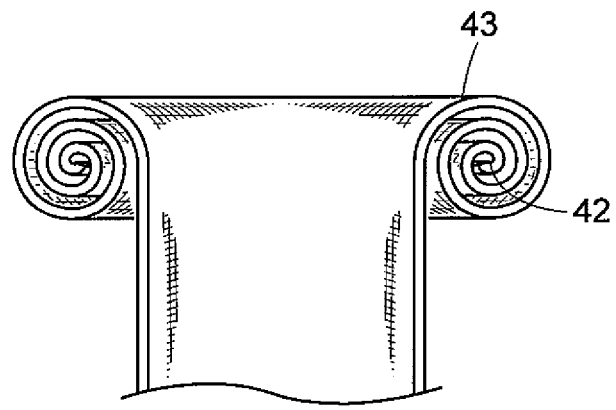
Figure 14:
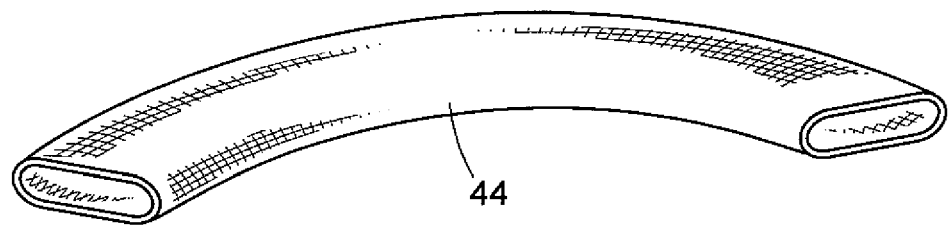
FIG. 14 illustrates a flattened tubular mesh.

Mesh may be fabricated in tubular form by weaving, knitting or braiding processes. (See FIGS. 9A-9D.) As with flat mesh materials, these tubular structures can incorporate multiple strand materials, process variations which produce a wide range of densities and strengths as well as three dimensional configurations. Rounds (FIG. 13 illustrating woven round tubular mesh 38), ovals and flattened tubular forms (FIG. 14 illustrating woven, flattened tubular mesh 44) are but a few examples and others will be apparent to those having skill in the art. These forms of mesh can also be sintered, filled or the like as previously described. One or more than one form may be inserted within the hollow core of another as illustrated in FIG. 13A which depicts a coaxial arrangement of cylindrical mesh tubes 38 and 39. Tubular mesh structures can also be combined with rolled and compacted mesh structures in various configurations as will be apparent to those skilled in the art based on the disclosures herein. A cylindrical mesh tube can also be rolled down upon itself to form a ring-like structure 40 or 41 as shown in FIGS. 13B-1 and 13B-2, respectively. It too can be rolled around an optional core element as shown in the section view 13B-3 illustrating core element 42 and mesh 43.

Flattened tubular mesh could be made by weaving, braiding or knitting to produce a flat, hollow cable or strap which additionally can be combined with many other components to form implantable medical devices. FIG. 14 shows a flattened tubular mesh 44 in its simplest form.

A section of mesh 44, sealed at one end can form a packet for containing medication and this can be used in the manner described in U.S. Pat. No. 6,916,483. The mesh structure permits body fluids to act upon the contents yet will contain them in a volume for implantation at a desired location in the body or in another implant. FIG. 14A illustrates this concept. The open end can be sealed intraoperatively using heat, adhesives, sutures or the like. Heating elements 45 and 46 are illustrated. These are moved in the directions of arrows 45A and 46A to seal one end 47. In an alternate embodiment both ends 47 and 48 can be sealed before implantation in a patient.

Figures 2, 14B:
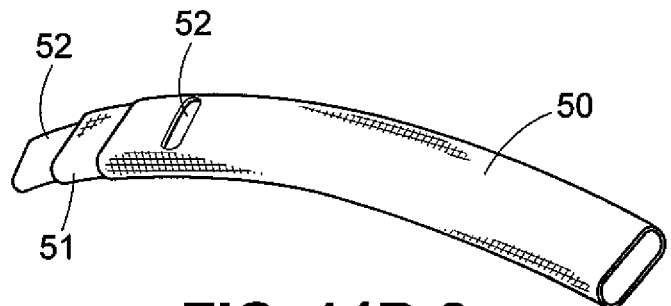
Figures 3, 14B:
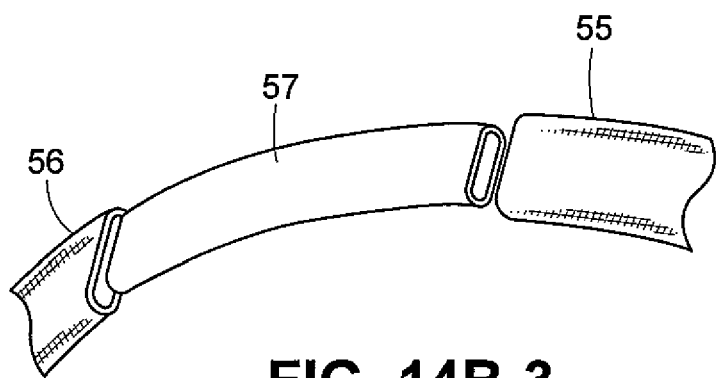
Figures 4, 14B:
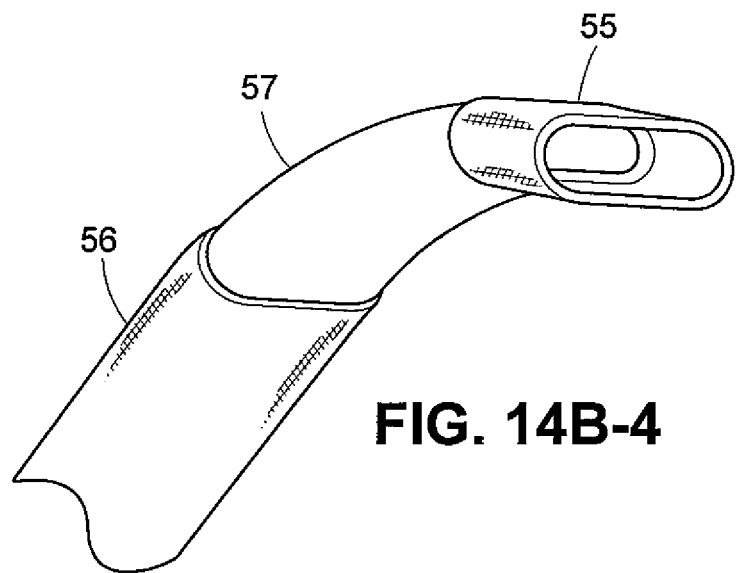

FIGS. 14B-1 and 14B-2 illustrate a multi-component flattened tubular mesh construct. Outer layer 50 and intermediate layer 51 are flattened tubular mesh with a core strip 52 comprising a solid material or mesh. These components can be selected to provide strength, stiffness, a targeted resorption profile, tissue ingrowth properties, etc. In a variation of this embodiment, one end of the outer member is partially cut away; the other forms a flattened tubular pocket. Such a construct can be slipped over the end of a segmentally resected rib, seating the rib in the pocket. This concept can also be applied to any fractured or incised bone. Alternatively, an open end of the flattened tubular mesh can be slipped over the end of the segmentally resected rib. The opposite end can then be secured to the other end of the rib segment thereby bridging the resection and restoring continuity to the chest wall. In another variation, if the resected rib segment or an allograft is available, either of these may be inserted into just the outer member to achieve fusion as well. Accordingly, an example of an orthopedic implant is described which is comprised of a mesh material shaped in the form of a structure for repairing a bone. This is illustrated in FIGS. 14B-3 and 14B-4 where sleeves 55 and 56 are slipped over each end of the resected rib segment 57. This can be reimplanted into the chest wall defect to achieve fusion.

Figure 14C:
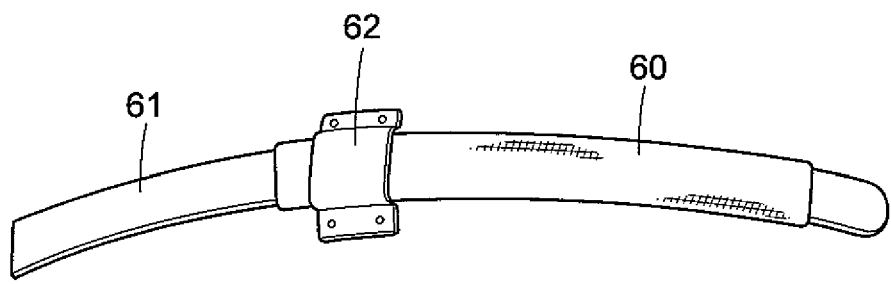
FIG. 14C illustrates a flattened tubular mesh with a movable member and a means of affixing the member relative to the mesh.
Figures 1, 14D:
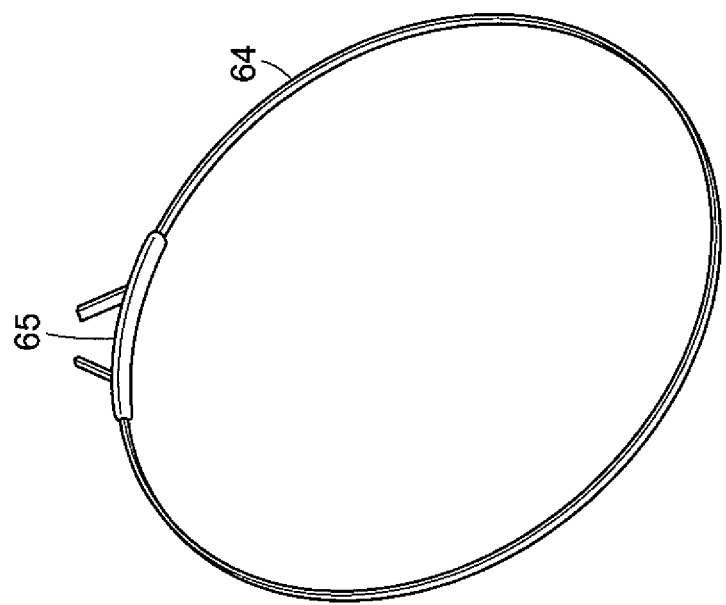
Figures 2, 14D:
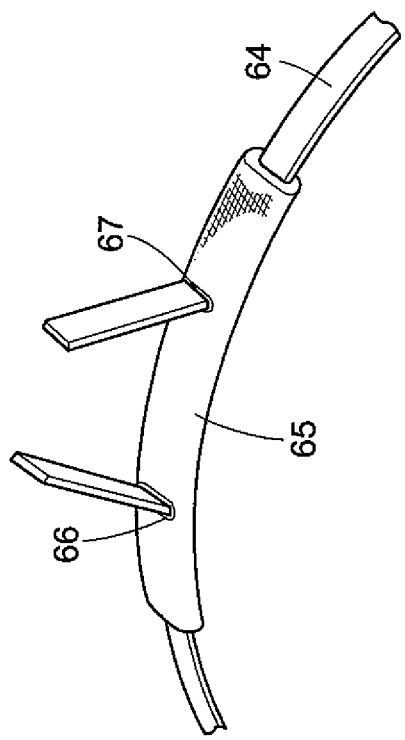

In a multi-component tubular mesh construction, the members can also be designed to be moveable relative to one another as shown in FIGS. 14C through 14D-3. FIG. 14C illustrates an outer flattened tubular member 60 which can be fixed in position. The inner mesh strap 61 can be attached to tissue (hard or soft) and slid into or out of the outer member 60 which can be fixed by various means, for example, bracket 62, thereby moving one tissue fixation point relative to the other. FIGS. 14D-1 and 14D-2 depict an inner mesh member 64 (cable or flat mesh) formed into a loop. Each end of this inner member is inserted through an opposite end of a flattened tubular mesh member 65 and then exits through lateral slots 66 and 67. Either or both ends of the inner member 64 can then be pulled through the outer member 65 to decrease the size of the inner loop. FIG. 14D-3 illustrates a single mesh strap 68 with a fastener 69 on one end. The free end of the mesh strap 68 is inserted through the slot in the fastener forming a loop, and by pulling on this end, the loop can be tightened.

Figures 1, 14E:
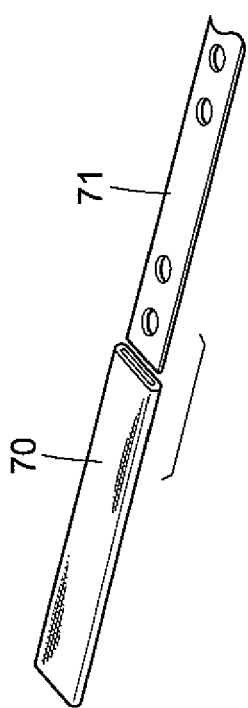
Figures 3, 14D:
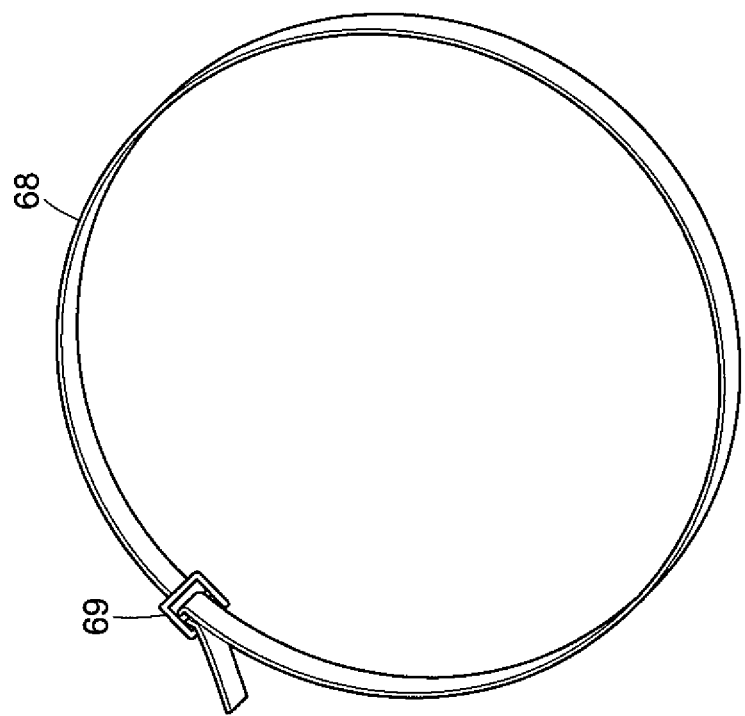
Figures 2, 14E:
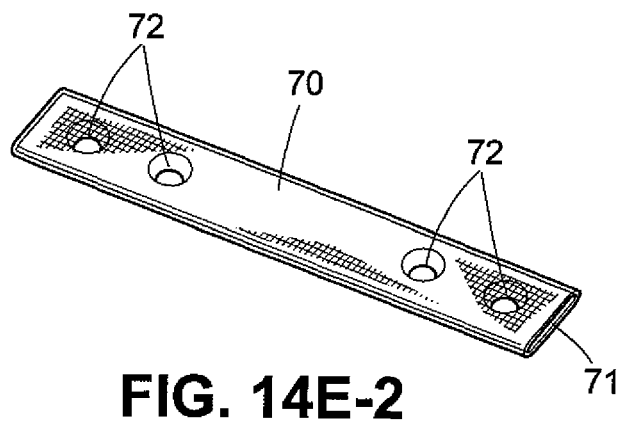

Flattened tubular mesh can also be used as an outer covering for a bone plate. The addition of this outer mesh cover can add strength, stiffness, tissue ingrowth properties, the ability to deliver medication, etc. FIGS. 14E-1 and 14E-2 illustrate this embodiment. These figures show the mesh 70 being perforated after being drawn over the bone plate structure 71 to expose the fastener holes 72. This perforation process can be performed with a heated punch to fuse, at least partially, the mesh to the plate and/or to fuse the edges of the holes to the mesh 70. The bone plate structure 71 can be comprised of a solid material or it can be comprised of mesh material which is the same as or different from mesh 70. For example, the bone plate structure 71 can be a filled and/or laminated mesh, a sintered mesh, a mesh strap or other mesh of the types described herein. It could also be a solid metal or plastic or a combination thereof or a combination of solid material and mesh material (e.g., a laminate) and it could be comprised of a resorbable, non-resorbable or a combination of resorbable and non-resorbable materials.

Other bone plate embodiments are illustrated in FIGS. 14E-3, E-4 and E-5. Each figure illustrates a section view of bone plate structure 71. In FIG. 14E-3, mesh material 73 is laminated to the top surface of bone plate structure 71. In FIG. 14E-4, mesh material 74 is laminated to the bottom surface of bone plate structure 71. And in FIG. 14E-5, mesh material 73 is laminated to the top surface and mesh material 74 is laminated to the bottom surface of bone plate structure 71.

Figure 15:
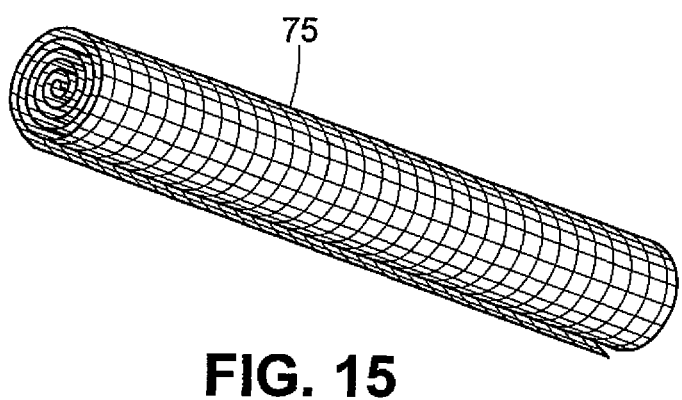
FIGS. 15 and 15A illustrate rolled mesh tubes with and without a core.
Figures 3, 14E:
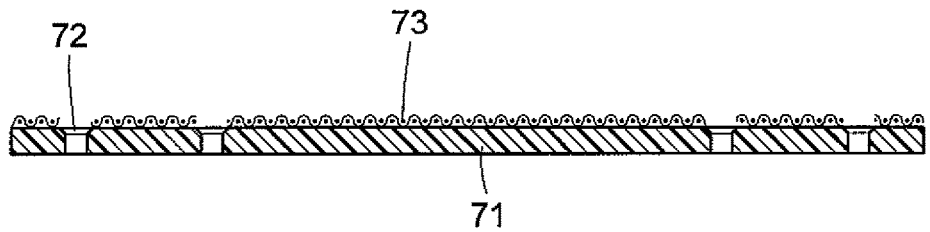
Figures 4, 14E:
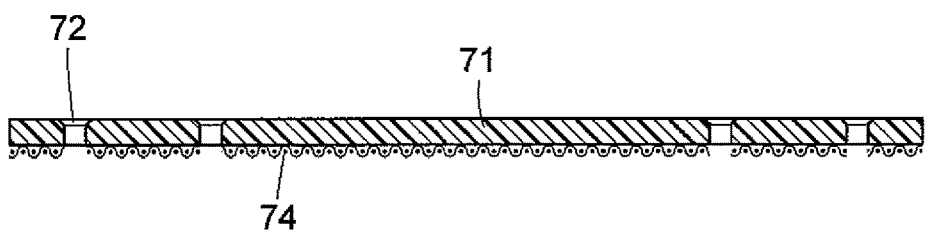
Figures 5, 14E:
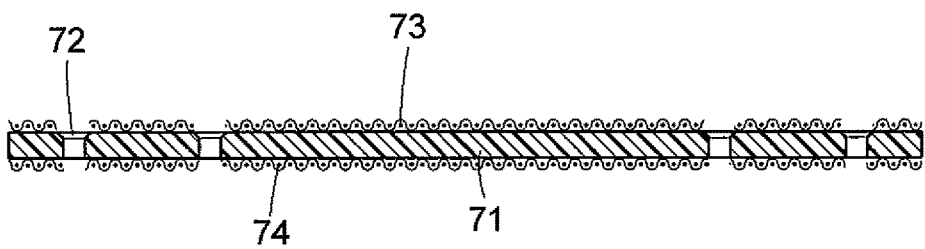
Figure 15A:
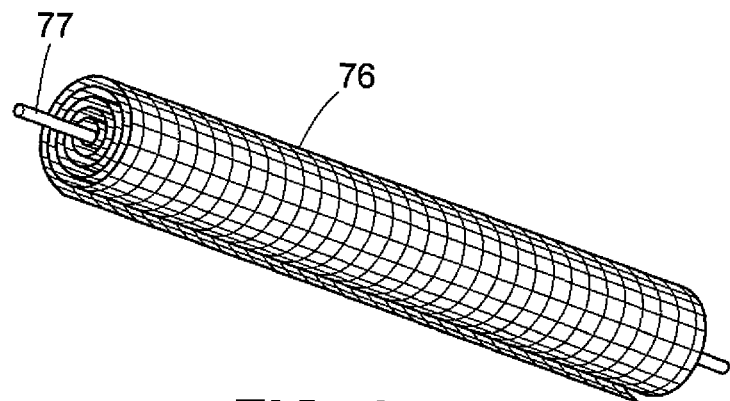

Tubular mesh structures may also be created by rolling up sheets of mesh. These can be single sheets, laminated sheets, sintered sheets or filled sheets or any combination thereof. A shaped core can be used in the process and this core may become part of the implant or may only be used for a portion of the fabrication process. This core can be solid, tubular or shaped, and it can be comprised of any implant materials known in the art. The core can be a composite of various implant materials and it may also take the form of a partial core if required. It is also possible to roll the mesh sheets with no core. Afterwards the rolled construct can be formed into a final cross-sectional shape using heat and/or pressure, adhesives, filling material, any flowable material that can be hardened by curing, etc. The orientation of the mesh strands relative to the rolling direction can be varied to produce different mechanical properties of the finished tubular form. Similarly, the orientation of the rolling direction relative to the edge of the sheet can greatly influence the mechanical properties of the finished tubular form. FIG. 15 illustrates a tube 75 rolled parallel to one of the strand directions and parallel to the edge of the mesh sheet. In the finished form, the mechanical properties will be uniform over the length of the tube. FIG. 15A shows a mesh sheet 76 rolled around a core 77.

Figure 16:
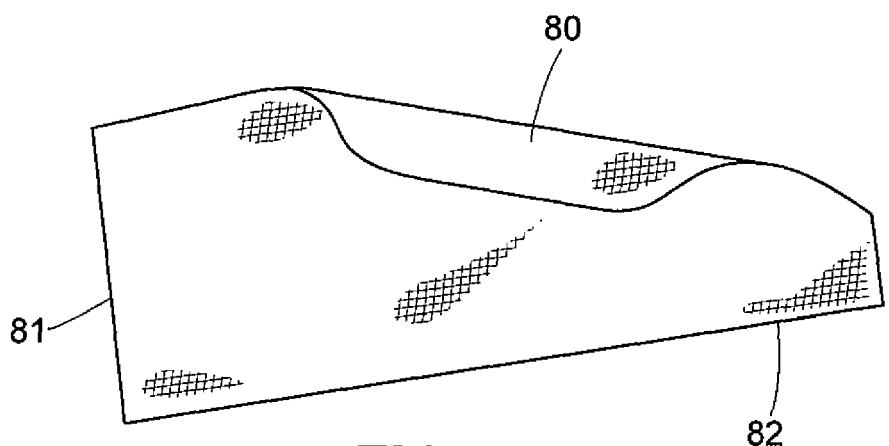
FIG. 16 illustrates a diagonally rolled mesh.
Figure 16A:
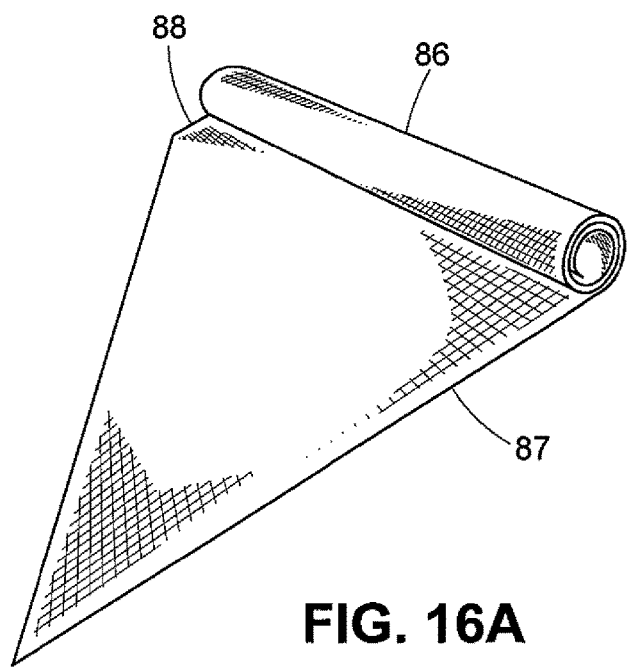
FIG. 16A illustrates a rolled pre-shaped mesh sheet.

FIG. 16 illustrates a mesh 80 rolled diagonally with respect to the edges of the sheet 81 and 82. When rolling is complete, a tube will be formed and the middle of the tube will have the greatest number of mesh layers. This number will steadily decrease as one moves from the middle toward either end of the tube. In this way, a variable stiffness mesh tube may be created. The ends of the tube can be cut square if desired. Furthermore the tube can be sectioned at any point to create the desired properties at an end. Obviously this concept can be carried further by shaping the mesh sheet prior to rolling. In a simple embodiment of this concept, consider FIG. 16A. The sheet of mesh 86 in this case is essentially the full sheet from FIG. 16, cut diagonally with one corner truncated. When this shaped sheet is rolled, the result will be a tubular member with a stiffness that decreases from edge 87 to edge 88.

Figures 1, 16B:
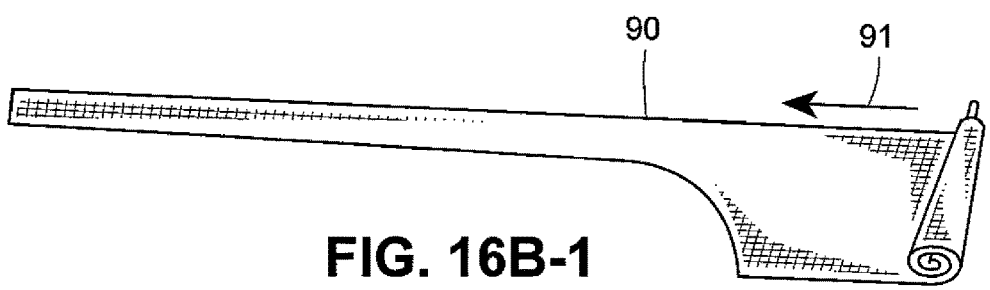
Figures 2, 16B:
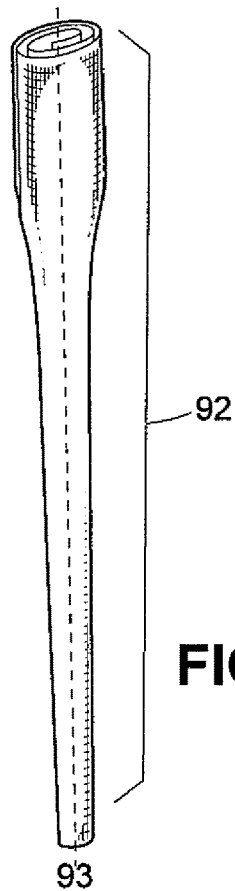
Figures 3, 16B:
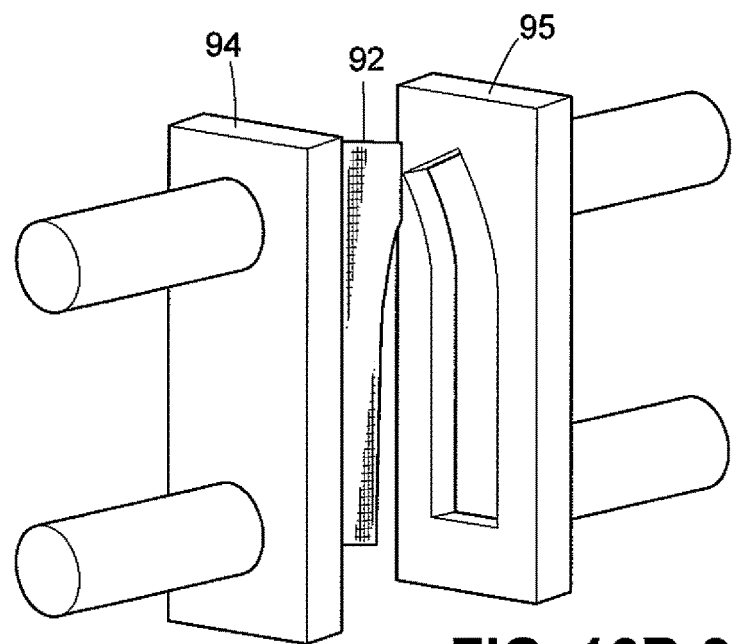

FIGS. 16B through 16E illustrate the use of a rolled, pre-shaped sheet as part of a larger process to produce a more complex shape. The process starts with a pre-cut or pre-shaped sheet of mesh 90 that is rolled lengthwise (FIG. 16B-1) in the direction of arrow 91. The result is a wrapped preform 92 with an axis of symmetry 93 (FIG. 16B-2). This preform is then placed between two platens 94 and 95 (FIG. 16B-3). Each platen has a cavity conforming to half of the final shape of the implant. Heat and/or pressure is used to compress and/or sinter the preform to the desired final shape—in this case a hip stem 96 (FIG. 16B-4). Because this final shape is rigid, it can be machined subsequently if required. Accordingly, an example of an orthopedic implant is described which is comprised of a mesh material shaped in the form of a structure (a prosthesis) for replacing a bone and/or a joint.

Figures 1, 16C:
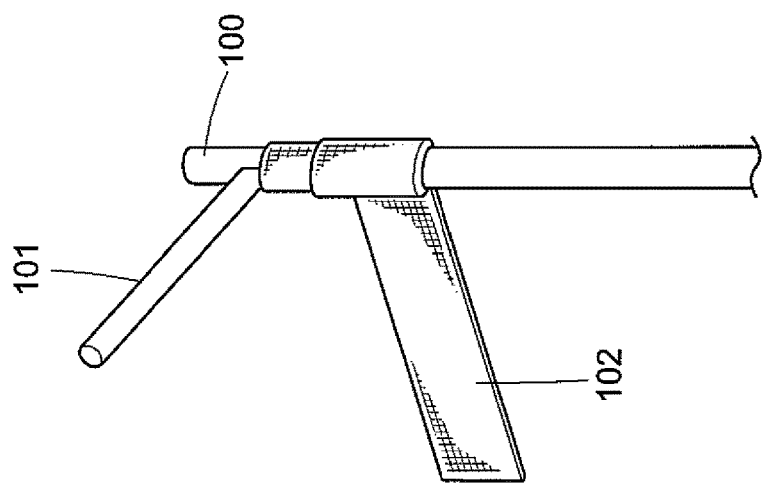
Figures 4, 16B:
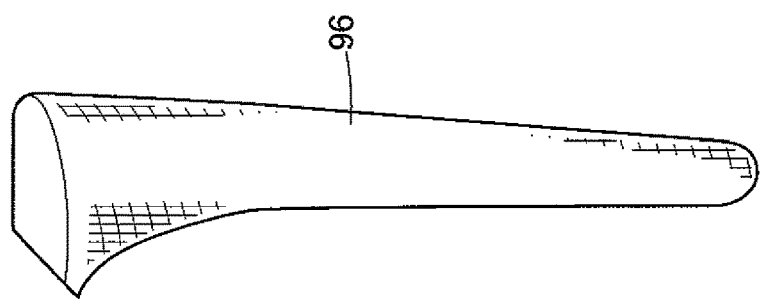
Figures 2, 16C:
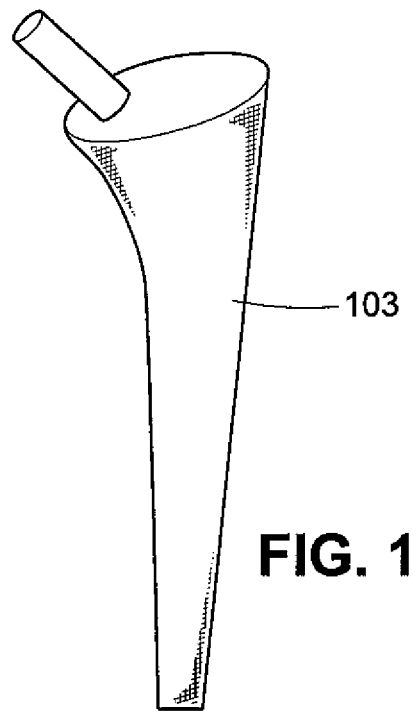
Figures 3, 16C:
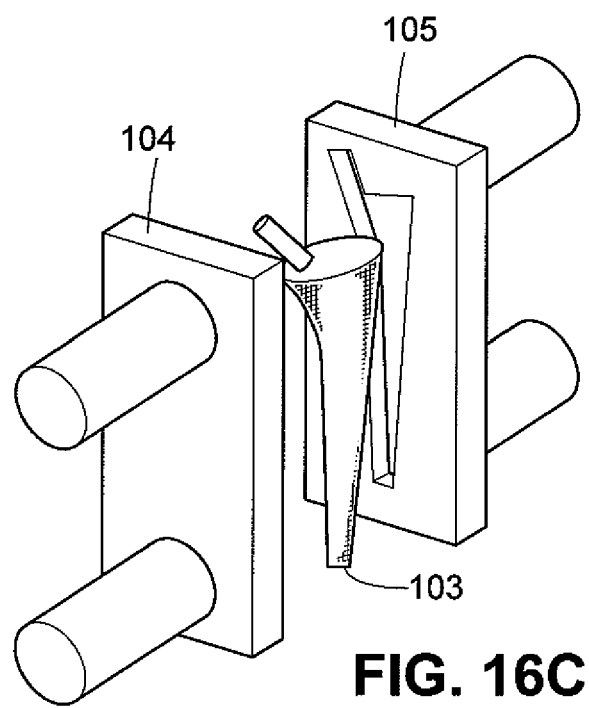
Figures 4, 16C:
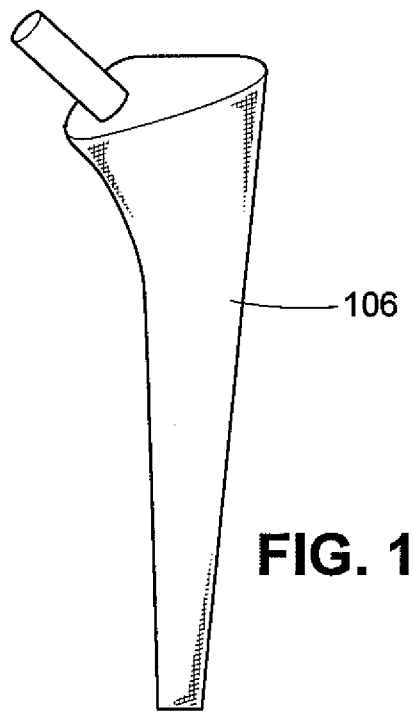

FIGS. 16C-1 through 16C-4 depict a different use of mesh to form a complex implant shape—in this case another hip stem. In this embodiment, a core comprised of a main shaft 100 and arm 101 is wrapped by a mesh strip 102 (FIG. 16C-1). This process proceeds much as one would tape an ankle or wrist, until the desired intermediate shape 103 is achieved (FIG. 16C-2). As in the previous example, the intermediate shape 103 is pressed between two shaped platens 104 and 105 (FIG. 16C-3) to achieve the final implant 106 (FIG. 16C-4).

Figure 17:
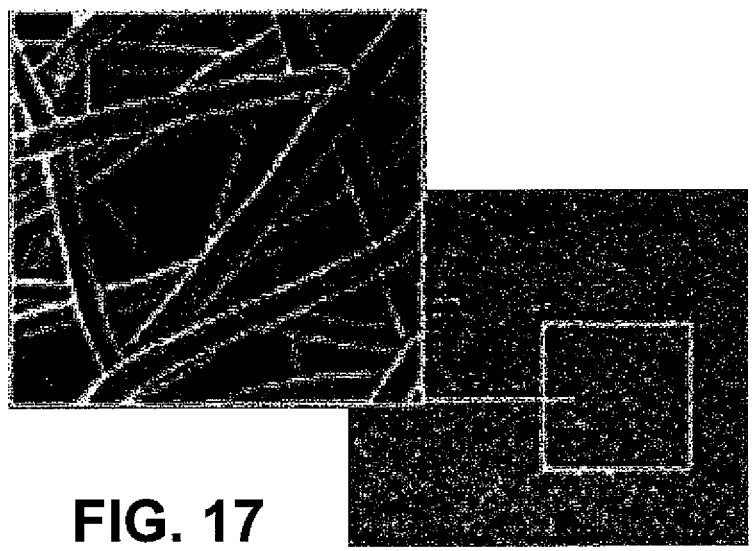
FIG. 17 illustrates the structure of a compressed sintered mesh.
Figure 18:
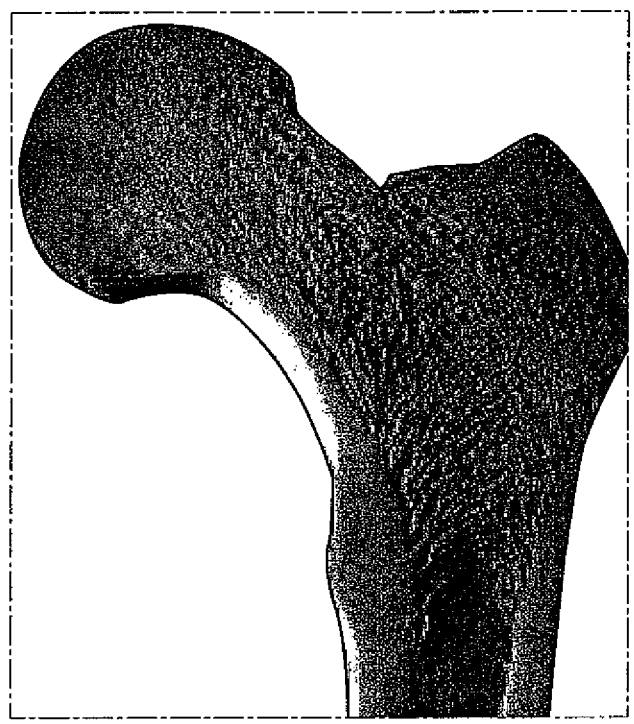
FIG. 18 illustrates cancellous bone of the femur.

More complex three-dimensional shapes can be formed by compacting the implantable mesh, similar to wadding up a piece of paper to throw in the trash. This can be done with single sheets, laminated sheets, rolled sheets, sintered sheets or filled sheets of mesh, or any combination thereof. Once the mesh is compacted into the desired shape, it can be locked in place by sintering and/or filling the strands. While a hip stem is illustrated, obviously this process could be used to produce a wide range of implants including bone plates, screws, rods, etc. The resulting three-dimensional structure of a compressed, sintered mesh (FIG. 17) is quite similar to that of cancellous bone (FIG. 18). Additionally, it is possible to coat this three dimensional mesh structure with other implant materials to provide an outer layer which is not mesh based.

Figure 19:
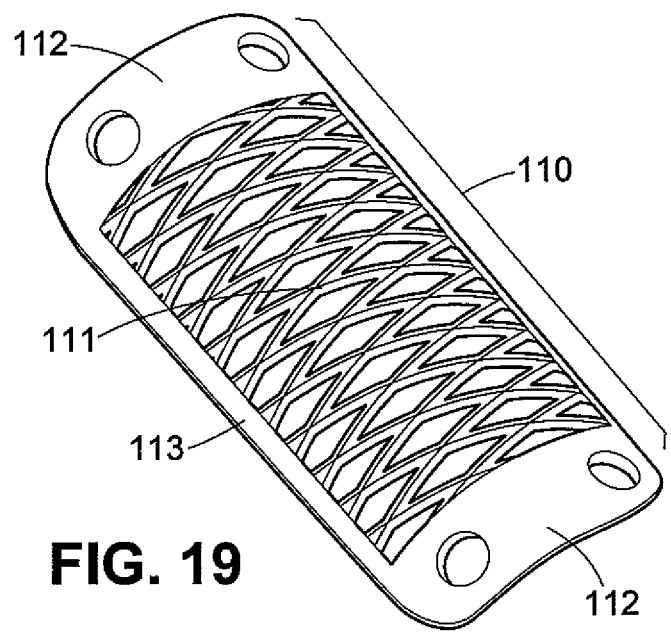
FIG. 19 illustrates a bone plate with a mesh central section.

Implantable mesh can be combined with other components to form a complete implant. FIG. 19 illustrates a bone plate 110 with a mesh central section 111, solid ends 112 for attachment to the bone and optional sides 113. Bone plate 110 can be manufactured by, for example, cutting a piece of mesh to approximately the shape and size of bone plate 110, filling the ends and side with a curable, flowable filling material and then curing the filling material. An alternative embodiment could be made without sides 113. Moreover, the ends and/or sides of bone plate 110 can be made of a material which softens on heating so that it can be conformed to the shape of the operating site of the patient. Then it would harden and retain its shape at body temperature. If the central section was filled with a bioresorbable material (not shown), it would initially be stiff but then would gradually transfer the mechanical load to the bone as the bioresorbable material degrades. The result would be an implant of reduced residual mass that would prevent stress shielding. The addition of bioresorbable filling material would also allow the implant to be heated to the softening point of the bioresorbable material for intraoperative contouring of the implant to the bone surface.

Figure 20:
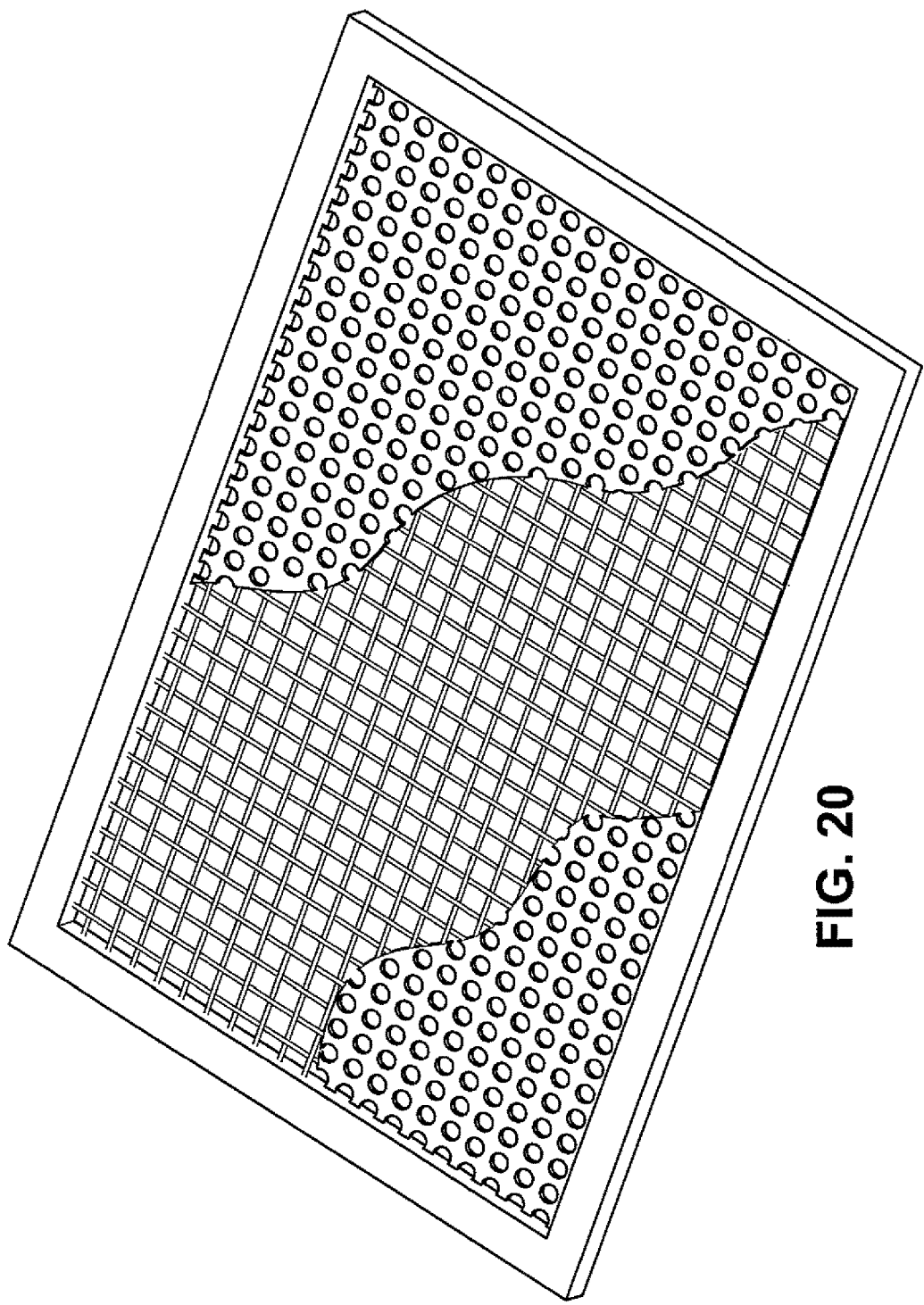
FIG. 20 illustrates a woven mesh that has been fused and perforated.

The mesh material also can be perforated. The perforation process can be combined with heat to fuse the perforated edges to prevent fraying or loosening of the fibers or strands. FIG. 20 illustrates this concept.

Mesh structures provide a means of producing surgical and orthopedic implants with enhanced properties. They represent a method of combining a wide range of existing implant materials in new ways to maximize their advantages and minimize their individual limitations. Strands of various materials can be interwoven at the mesh level. Various fabrication methods (e.g., weaving, knitting, braiding and perforating) can create mesh with a wide range of physical properties. Layers of different mesh can be laminated together to produce a hybrid implant material with properties precisely tailored to the clinical indication. These mesh structures can be further reinforced by sintering the strands to prevent movement and/or by encapsulating them in another material. In this manner, an implant can be made with properties not found in the current selection of biomaterials. Implants for fracture fixation could be made with the required initial strength but also with the ability to partially or completely resorb preventing stress shielding, minimizing the amount of residual foreign material in the patient and reducing the number of second (removal) surgeries. Reconstructive implants could be made with internal structures similar to cancellous bone, thus offering a better combination of strength, resiliency and reduced weight. Surgical meshes for muscle, ligament or tendon repair and/or reattachment to bone can be wholly or partially resorbable and offer the ability to deliver antibiotics or other medications to the local surgical site. The exposed surfaces of implants could be designed either to encourage or discourage the ingrowth of hard or soft tissues. The net result is a new class of biomaterials with enhanced mechanical and biological properties.

What is claimed is:

1. An orthopedic implant comprised of a mesh material and a bone plate, wherein the mesh material is provided as a sleeve having a flattened tubular construction adapted to be slidably affixed as an outer covering around at least a portion of the bone plate, the flattened tubular construction being of a fairly uniform width throughout to accommodate a defined width of the bone plate therein, and wherein the mesh material comprises at least one perforated portion formed at a location corresponding to a fastener hole of the bone plate after being slidably affixed to the bone plate, the formed perforated portion of the mesh material at least partially fused to an edge of the fastener hole.

2. The orthopedic implant of claim 1 wherein the mesh material is comprised of at least two different strand structures having the same or different compositions.

3. The orthopedic implant of claim 2 wherein the at least two different strand structures are selected from the group consisting of monofilament, braided, yarns, threads, hollow tubes, flat strips, solid ovals, hollow ovals and solid rounds.

4. The orthopedic implant of claim 2 wherein the compositions are selected from the group consisting of resorbable materials, non-resorbable materials and resorbable and non-resorbable materials.

5. The orthopedic implant of claim 1 wherein the mesh material is comprised of strands having interstices therebetween.

6. The orthopedic implant of claim 5 further comprising medication contained within at least some of the interstices.

7. The orthopedic implant of claim 5 wherein at least some of the interstices are filled with a biocompatible material.

8. The orthopedic implant of claim 7 further comprising medication contained within at least some of the interstices.

9. The orthopedic implant of claim 7 further comprising medication contained within at least some of the biocompatible material.

10. The orthopedic implant of claim 5 wherein at least some of the strands are tubular strands.

11. The orthopedic implant of claim 10 further comprising medication within the tubular strands.

12. The orthopedic implant of claim 1 wherein the mesh material is at least partially fused to the bone plate.

13. The orthopedic implant of claim 1 wherein the mesh material is comprised of strands having interstices therebetween and at least some of the interstices are filled with a biocompatible material or medication or a biocompatible material and medication.

* * * * *